United States Patent [19]

Hall et al.

[11] 4,187,856
[45] Feb. 12, 1980

[54] HIGH-SPEED TRANSMISSION OF BLOOD STREAM GASES

[75] Inventors: Lawrence G. Hall, Creve Ceour, Mo.; Wayne J. Whistler, Glendora, Calif.

[73] Assignee: The Perkin-Elmer Corporation, Norwalk, Conn.

[21] Appl. No.: 893,032

[22] Filed: Apr. 3, 1978

[51] Int. Cl.² ............................................. A61B 5/00
[52] U.S. Cl. ................................. 128/635; 23/232 R; 73/40.7
[58] Field of Search .......................... 128/2 E, 2.1 E; 23/232 R; 250/281, 489; 422/83; 73/40.7, 421.5 R

[56] References Cited

U.S. PATENT DOCUMENTS

| 3,572,315 | 3/1971 | Cullen | 128/2 E |
| 3,645,127 | 2/1972 | Mongodin et al. | 73/40.7 |
| 3,926,561 | 12/1975 | Lucero | 422/83 |
| 4,004,882 | 1/1977 | Byrne et al. | 422/83 |

*Primary Examiner*—William E. Kamm
*Attorney, Agent, or Firm*—Salvatore A. Giarratana; Francis L. Masselle; Edwin T. Grimes

[57] ABSTRACT

The various gases in the blood stream are analyzed by a mass spectrometer coupled to the catheter having on its distal end a membrane that passes the gases but not the blood. A "carrier" gas, such as helium, introduced under a small pressure through a small tube within the catheter lumen and into the area behind the membrane will produce a viscous flow that greatly speeds the gases to the mass spectrometer. The carrier gas is extracted prior to its arrival at the mass spectrometer.

1 Claim, 1 Drawing Figure

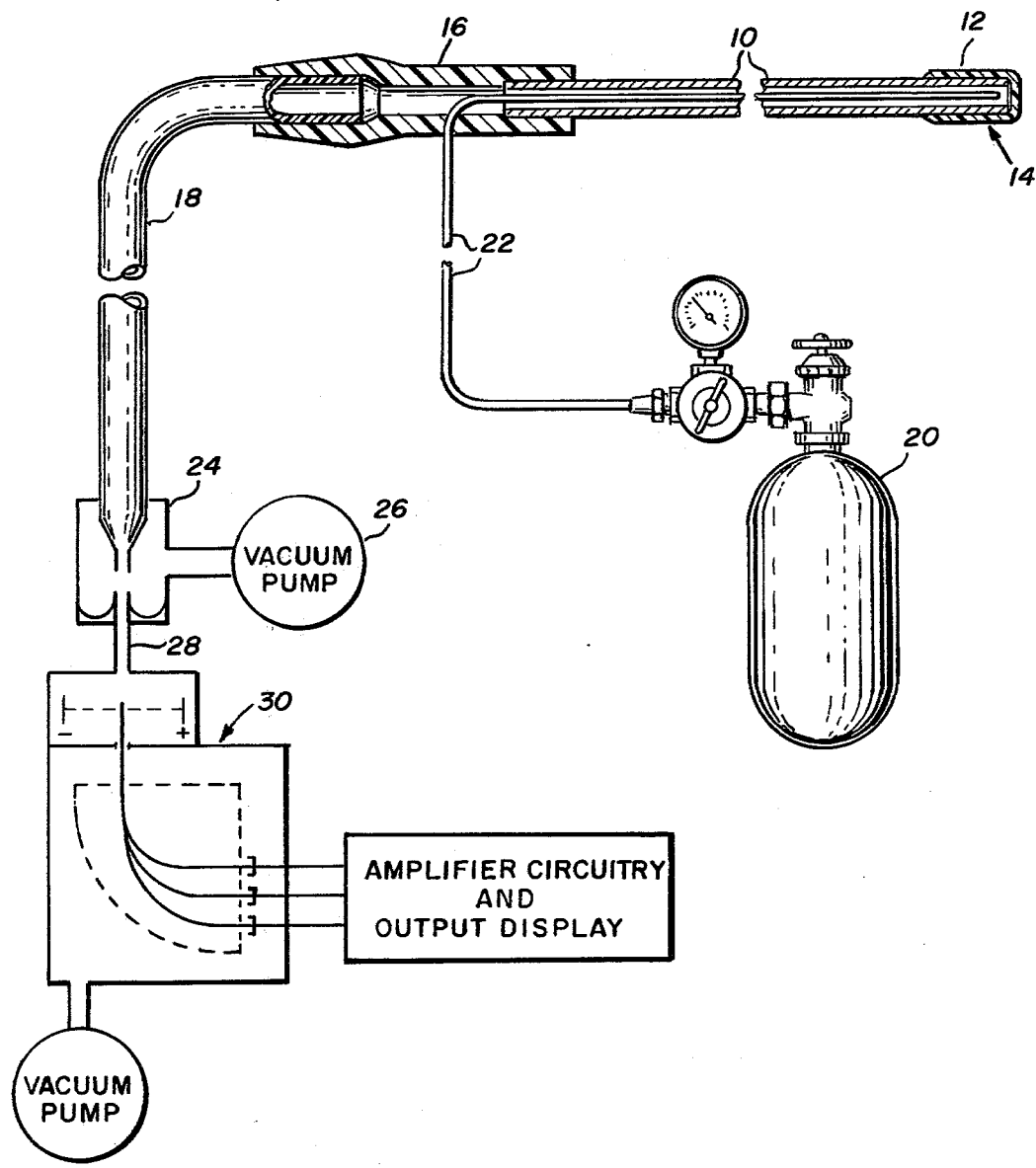

HIGH-SPEED TRANSMISSION OF BLOOD STREAM GASES

SUMMARY OF THE INVENTION

A knowledge of the quantity of each of the gases in the human blood stream is a valuable medical diagnostic tool and a means for continually monitoring the arterial system and analyzing the blood stream gases of one or more patients, for example, in a post-operative intensive care unit, would be an extremely valuable tool for determining the condition of patients' respiratory systems and would provide an early warning of possible malfunctioning.

At the present time, the analysis of the blood stream gases is made by withdrawing an arterial or venous blood sample and, without exposing the sample to the atmosphere, expose the blood to a gas sample input leak of a mass spectrometer. It is apparent that a much more accurate method of obtaining a sample of blood stream gases would be to insert a catheter into the blood stream to "sniff" gas samples. While such a system is acceptable for use on a single patient where the catheter can be placed very closely to the mass spectrometer, it is not practical where the simultaneous monitoring of the respiratory systems of several patients because of the exceedingly long time required for the extremely small samples of the blood gases to drift by molecular flow from the distal end of the catheter to the mass spectrometer. If the blood gases could pass from the catheter to the spectrometer at a much higher speed, it would then be possible to monitor the respiratory systems of several patients with a single mass spectrometer.

The present invention provides a method for very rapidly carrying blood gas samples from the catheter to the mass spectrometer. It has been computed that, without the present invention, a sample of blood gas would drift by molecular flow over a distance of sixteen meters in approximately fifteen minutes, a period of time obviously too long to detect a possible respiratory malfunction. By using the invention, samples of blood gases will flow from a catheter to a mass spectrometer sixteen meters distant in approximately four seconds.

Briefly described, a catheter provided with a blood-blocking membrane at its distal end is equipped with a very small tube throughout its lumen and terminating in the area of the membrane. A "carrier" gas, such as helium, is introduced through the tube and against the interior surface of the membrane where it mixes with the blood gases passing through the membrane. The blood gases thus mixed with the carrier gas is now under a small pressure and passes by viscous flow at a relatively high speed through the tubing interconnecting the catheter with the sampling input leak of the mass spectrometer.

DETAILED DESCRIPTION OF THE DRAWING

The single FIGURE is a schematic drawing illustrating the principles of the invention and includes a cross-sectional drawing of a typical catheter with means for introducing a carrier gas.

DETAILED DESCRIPTION OF THE INVENTION

As shown in the figure, a catheter which comprises a metallic tube 10 with the open distal end sealed with a membrane 12. The membrane 12 is preferably of a material, such as Teflon, that is sufficiently porous to pass blood stream gases while resisting the passage of the blood. The catheter tubing 10 may have an outside diameter of approximately three millimeters and the wall thickness of approximately one-half millimeter and its distal end 14 is sufficiently sharp to enter into a human artery. While the illustrated catheter 10 is shown with the membrane 12 covering the entire distal end 14, other designs may be more effective, since catheters with means permeable to blood gases are known in the art. The proximal end of the catheter tube 10 is coupled into a tubing connector 16 which interconnects the catheter tube 10 to a gas transmission tubing 18.

In accordance with the invention, a "carrier" gas, such as helium, hydrogen, or other light gas, stored in a container 20 is admitted into the catheter tube 10 through a very small capillary tube 22. The capillary tube 22 enters the tube connector 16 and extends through the length of the lumen of tube 10 to terminate just short or membrane 12 at the distal end 14 of the catheter tube.

In operation, the carrier gas in the container 20 is metered into the capillary tube 22 at a pressure of about one atmosphere. The distal end 14 of the capillary tube 18 is inserted into an artery so that the membrane 12 will be positioned to sample the blood stream gases. These gases pass through the membrane 12 into the lumen of the catheter tube 10 where they are mixed with the carrier gas under pressure and forced through tubing 10, the gas transmission tube 18 and into a chamber 24 for the removal of the carrier gas from the gas mixture. While it is not essential to remove the carrier gas, it is desirable to do so, preferably by techniques well-known to the art of gas chromatography, such as by a Ryhage separator or palladium hydrogen extractor. The chamber 24 illustrated in the drawing is typically a Ryhange separator which allows the lightweight gases, such as helium or hyrogen, to expand rapidly and be carried away by a vacuum pump 26, while the heavier blood gases that expand less, enter the input sampling leak 28 of a mass spectrometer 30. Spectrometer 30 forms no part of the present invention but merely illustrates a valuable means for determining the proportions of each blood gas sampled by the catheter and rapidly transmitted over a relatively long distance for analysis.

What is claimed is:
1. A system for providing blood gas specimens from blood vessels to a gas analyzer comprising:
   a catheter having an outside diameter of approximately three millimeters comprising a distal end and a proximal end, said distal end being sufficiently sharp to enter a human blood vessel, said distal end having an opening sealed with a membrane impervious to blood,
   a first conduit interconnecting the proximal end of said catheter and the gas analyser,
   a capillary tube extending through the lumen of said catheter,
   a carrier gas source containing a carrier gas substantially lighter than said blood gas,
   one end of said capillary tube terminating at the distal end of said catheter,
   a second conduit connecting said carrier gas source to the other end of said capillary for admitting a carrier gas into said capillary tube extracting means connecting to said first conduit for causing said carrier gas to expand substantially more than said blood gas,
   said extracting means including a vacuum pump for carrying away said carrier gas.

* * * * *